US00PP36876P2

(12) United States Plant Patent
Lim

(10) Patent No.: US PP36,876 P2
(45) Date of Patent: Aug. 5, 2025

(54) ***HIBISCUS* PLANT NAMED 'ALTpinky'**

(50) Latin Name: *Hibiscus rosa-sinensis*
Varietal Denomination: ALTpinky

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,320

(22) Filed: Jan. 15, 2025

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

PP24,468 P3 * 5/2014 Dupont, Sr. ..... A01H 6/608 Plt./257

* cited by examiner

*Primary Examiner* — Karen M Redden
(74) *Attorney, Agent, or Firm* — Cassandra Bright

(57) ABSTRACT

A new and distinct cultivar of *Hibiscus* plant named 'ALTpinky' is disclosed, characterized by pink flowers with a red halo around a darker red center. Plants are dwarf, reaching about 2 feet in a 2-gallon pot. Petals are thick and moderately rugose. The new variety is a *Hibiscus*, typically produced as an ornamental plant.

1 Drawing Sheet

Latin name of the genus and species: *Hibiscus rosa-sinensis*.

Variety denomination: 'ALTpinky'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Aug. 22, 2016.

The seed parent is the unpatented *Hibiscus rosa-sinensis* 'Love Story'. The pollen parent is an unreleased proprietary variety of *Hibiscus rosa-sinensis*. The new variety was identified and selected as a potentially interesting selection in July of 2019. Selection was made at a commercial nursery in Vista, California.

Asexual reproduction of the new cultivar 'ALTpinky' was first performed Jul. 20, 2019 in Vista, California, by vegetative cuttings. Subsequent propagation has shown that the unique features of this cultivar are stable and reproduced true to type in successive generations.

SUMMARY OF THE INVENTION

The cultivar 'ALTpinky' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTpinky'. These characteristics in combination distinguish 'ALTpinky' as a new and distinct *Hibiscus* cultivar:

1. Pink flowers with a red halo around a darker red center.

2. Thick petals
3. Dwarf plant about 2 feet tall in a 2-gallon container.
4. Large, cordate foliage.

PARENT COMPARISONS

Plants of the new cultivar 'ALTpinky' are similar to the seed parent, in most horticultural characteristics. However, characteristics of the new cultivar differ in the following:

1. The new cultivar is much shorter than plants of the seed parent.
2. Flowers of the new cultivar are single; flowers of 'Love Story' are double.
3. Flower color of the new cultivar is pink with a red halo around a darker red center; flower color of 'Love Story' is red and white.

Plants of the new cultivar 'ALTpinky' are similar to the pollen parent, in most horticultural characteristics. However, characteristics of the new cultivar differ in the following:

1. The new variety is much shorter than plants of the pollen parent.
2. Flower color of the new cultivar is different than flower color of the pollen parent.

COMMERCIAL COMPARISON

Plants of 'ALTpinky' are similar in some horticultural characteristics to the variety *Hibiscus* 'Erin Rachel', unpatented. The new variety, however, differs in the following:

1. Flowers of 'ALTpinky' are larger than flowers of 'Erin Rachel'.
2. Plants of 'Erin Rachel' are taller than plants of 'ALTpinky'.

3. Flowers of 'ALTpinky' are pink with a red halo around a darker red center while flowers of 'Erin Rachel' are bright orange blended into a pink and magenta center.
4. Foliage of 'ALTpinky' is larger than foliage of 'Erin Rachel'.

Plants of 'ALTpinky' are similar in some horticultural characteristics to the variety *Hibiscus* 'Adonicus Pink', unpatented. The new variety, however, differs in the following:

1. Flowers of 'ALTpinky' are larger than flowers of 'Adonicus Pink'.
2. Petal of 'ALTpinky' thicker and more ruguose than petals of 'Adonicus Pink'.

BRIEF DESCRIPTION OF THE PHOTOGRAPH

The accompanying photograph illustrates in full color a typical flower of 'ALTpinky' from a plant grown outdoors at a commercial nursery in Vista, California. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'ALTpinky' plant. This plant was grown at a commercial nursery in Vista, California. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTpinky'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 1.5 years old.

Growth habit: Compact.

Height: 50 cm.

Plant spread: 50 cm.

Branching characteristics: 2 to 4 breaks from a pinch, occurring at an average 45° angle.

Length of primary lateral branches: 20 to 50 cm.

Quantity of lateral branches: Each primary lateral branch has 4 to 8 laterals.

Characteristics of primary lateral branches:

*Diameter.*—Average range 11 to 17 mm.

*Color.*—New growth RHS Green 143A. Mature growth RHS Greyed-Green 197B, striated Grey-Brown N199A.

*Texture.*—New growth very sparsely hirsute, older growth striated.

Internode length: Average 2.4 cm.

FOLIAGE

Leaf:

*Arrangement.*—Alternate.

*Quantity.*—Average 12 to 20 per branch.

*Leaf internode.*—1 cm.

*Average length.*—9 to 12 cm, excluding petiole.

*Average width.*—9.5 cm.

*Shape of blade.*—Cordate.

*Apex.*—Acute.

*Base.*—Obtuse.

*Margin.*—Entire or irregularly and shallowly crenate.

*Aspect.*—Strongly undulating.

*Texture of top surface.*—Glabrous.

*Texture of bottom surface.*—Sparse and very short hirsute.

*Color.*—Young foliage upper side: RHS Green 139A. Young foliage under side: RHS Green 137A. Mature foliage upper side: RHS Green 139A. Mature foliage under side: RHS Green 137B.

*Venation.*—Type: Pinnate. Venation color, upper side: RHS Green 137B. Venation color, under side: RHS Green 138B.

*Petiole.*—Length: 2 to 2.9 cm. Diameter: 4 to 5 mm. Color: Near RHS Green 137A Texture: Densely short hirsute.

*Leaf stipule.*—Not observed.

FLOWER

Natural flowering season: Nearly year-round in Southern California.

Flower type and habit: Solitary, rotate.

*Single, double, multiplex.*—Single.

*Petals overlapping.*—Strongly overlapping.

Quantity of flowers: A plant of about 2 years old has approximately 30 open flowers at one time during Summer.

Rate of flower opening: 4 to 6 days from bud to fully opened flower.

Flower longevity on plant: 2 to 3 days.

Persistent or Self-Cleaning: Self-cleaning.

Bud:

*Shape.*—Ovate.

*Length.*—6 cm.

*Diameter.*—2.6 cm.

*Color.*—RHS Green 137D, lightly flushed Green 138C.

Flower size:

*Diameter.*—20 cm.

*Depth.*—10 cm.

Petals:

*Quantity.*—5.

*Arrangement.*—Whorled, strongly overlapping.

*Length.*—11 cm.

*Width.*—9 cm.

*Shape.*—Slightly asymmetrical broad spatulate.

*Apex.*—Obtuse rounded with irregular, shallow crenations.

*Base.*—Attenuate.

*Margin.*—Entire. Moderate undulation.

*Texture.*—Glabrous all surfaces. Strongly rugose top and bottom.

*Color*.—When opening, upper surface: RHS Red 46C. Large basal blotch (forming flower eye) with halo colored near Red 46A, interior Red 53A flushed Greyed-Purple N186C. When opening, lower surface: RHS Red 46C, basal area Red 47D. Fully opened, upper surface: RHS Red 51A with overlay 54B. Large basal blotch (forming flower eye) with halo colored near Red 46B, interior Red 53A flushed Greyed-Purple N186C. Fully opened, lower surface: RHS Red 46C, basal area Red 47D. Ratio of basal blotch/eye to petal size: Overall 30% of petal blade is blotched. Feathering: No significant feathering.

Sepals:

*Quantity*.—5.
*Length*.—2.5 cm.
*Width*.—1.3 cm.
*Shape*.—Oblanceolate.
*Margin*.—Entire.
*Apex*.—Acute.
*Base*.—Fused.
*Color*.—Upper surface: RHS Green 137C. Lower surface: RHS Green 137C.
*Texture*.—Upper surface: Softly pubescent. Lower surface: Very short hirsute.

Epicalyx:

*Quantity of bracts*.—6.
*Bract length*.—1.4 cm to 1.8 cm.
*Bract width*.—3 to 4 mm.
*Bract shape*.—Straplike.
*Bract margin*.—Entire.
*Color*.—Upper surface: RHS Green 137A. Lower surface: Near RHS Green 137B.
*Texture*.—Upper surface glabrous, lower surface non-pubescent rough.

Peduncles:

*Length*.—4 to 5 cm.
*Diameter*.—6 mm.
*Angle*.—Approximately 45° to the lateral branch.
*Strength*.—Strong.
*Texture*.—Sparsely hirsute.
*Color*.—RHS Green 137B.

Fragrance: Faint musty scent.

REPRODUCTIVE ORGANS

Stamens:

*Number*.—About 50 to 60.
*Filament length*.—10 mm.
*Filament color*.—Near Red 50C.

Anthers:

*Shape*.—Irregular sphere.
*Length*.—About 3 mm.
*Color*.—Near RHS Yellow 12B.
*Pollen color*.—Near RHS Yellow 12B.
*Pollen amount*.—Scant.

Pistil:

*Number*.—1.
*Length*.—10 cm.
*Style*.—Length: 8 cm. Color: Lower section near Red 53B, mid-section has spiraling lines of 54B. Uppermost ⅓ Red 54C.
*Stigma*.—Shape: Peltate. Color: Near RHS Red 53D.
*Ovary color*.—Near RHS Orange 27D.
*Ovary length*.—1.5 cm 7.
*Ovary width*.—8 mm.

OTHER CHARACTERISTICS

Seeds: Not observed.

Disease/pest resistance: Neither resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTpinky' as herein illustrated and described.

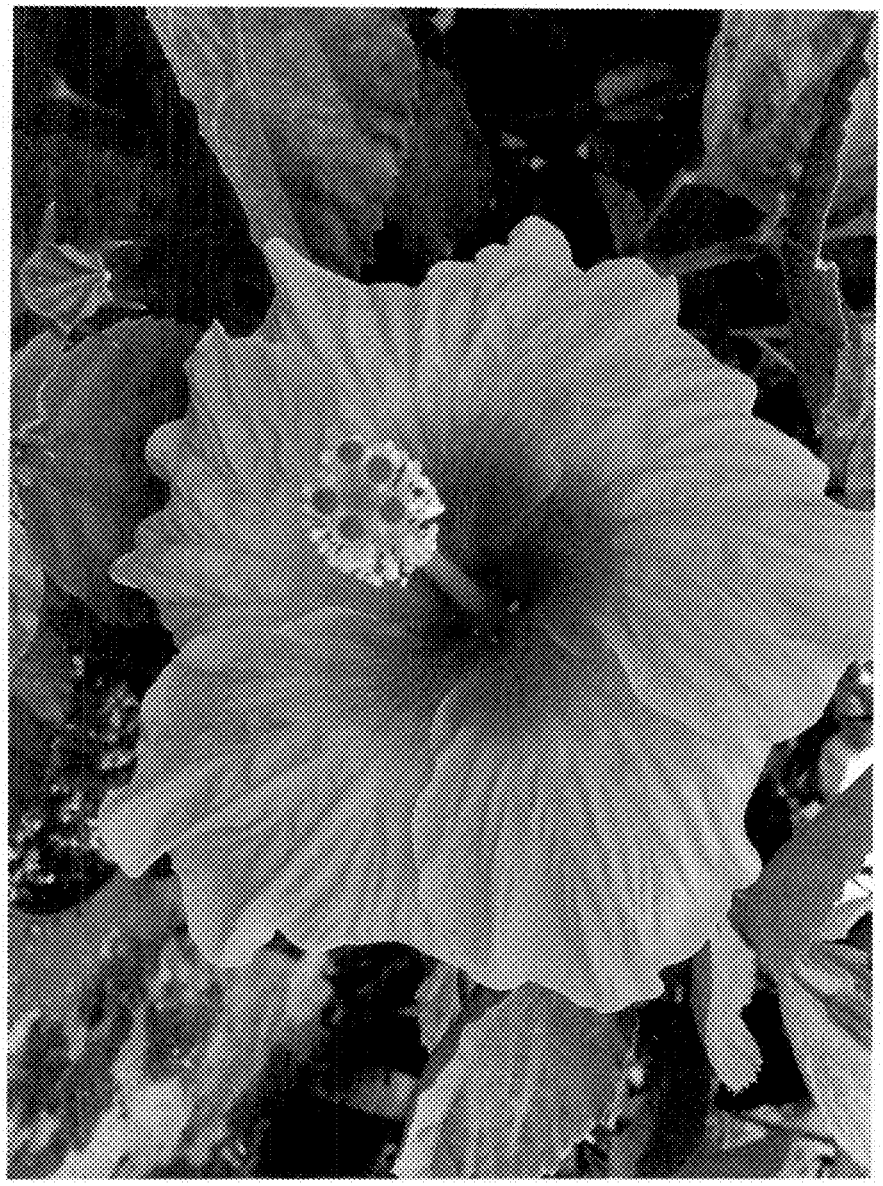

* * * * *